United States Patent [19]

Dazey et al.

[11] Patent Number: 5,252,710
[45] Date of Patent: Oct. 12, 1993

[54] PROCESS FOR MANUFACTURING VON WILLEBRAND FACTOR

[75] Inventors: Bernard Dazey; Mohamed Hamsany, both of Bordeaux; Gérard Vezon, Cursan, all of France

[73] Assignee: Association d'Aquitaine pour le Developpment de la Transfusion Sanguine et des Recherches Hermatologiques, France

[21] Appl. No.: 739,452

[22] Filed: Aug. 2, 1991

[30] Foreign Application Priority Data

Aug. 2, 1990 [FR] France .................. 90 09917

[51] Int. Cl.$^5$ .................. C07K 3/22; C07K 15/06
[52] U.S. Cl. .................. 530/383; 530/416
[58] Field of Search .............. 530/380, 383, 384, 412, 530/416

[56] References Cited

U.S. PATENT DOCUMENTS

| | | | |
|---|---|---|---|
| 4,170,590 | 10/1979 | Stephan et al. | 530/383 |
| 4,670,543 | 6/1982 | Bourgois et al. | 514/8 |
| 4,774,323 | 9/1988 | Newman et al. | 530/383 |
| 4,883,598 | 11/1989 | Riethorst et al. | 530/381 |

FOREIGN PATENT DOCUMENTS 2650393  3/1991  France .................. 530/383

OTHER PUBLICATIONS

British Journal of Haematology, vol. 43, issued 1979, Austen, "The Chromatographic Separation of Factor VIII . . . ", pp. 669–674.
DBA Abstract, PCT WO89-12065, Dec. 14, 1989.

Primary Examiner—Jeffrey E. Russel

[57] ABSTRACT

The invention relates to a process for manufacturing von Willebrand factor. This process comprises the selective adsorption of factor VIIIc on the gel of a first ion exchange chromatography column, the von Willebrand factor being contained in the non-retained fraction, and is characterized in that the non-retained fraction is treated so as to adsorb the von Willebrand factor selectively on the gel of a second chromatography column, the factor then being desorbed and being obtained with a very high purity. The invention enables a von Willebrand factor of very high purity, largely devoid of antihaemophilic factor VIIIc and of inactivators such as Tween and TNBP, as well as of the main plasma contaminants, to be obtained 10 Claims, No Drawings

PROCESS FOR MANUFACTURING VON WILLEBRAND FACTOR

CROSS REFERENCE TO RELATED APPLICATION

This application is related to Applicant's copending U.S. application Ser. No. 07/476,978 filed on Feb. 7, 1990.

BACKGROUND OF THE INVENTION

1. Field of the Invention

The invention relates essentially to a process for manufacturing von Willebrand factor having a very high purity, and to the von Willebrand factor thereby obtained as well as to a pharnaceutical composition containing it.

2. Description of the Related Art

Various processes for manufacturing von Willebrand factor are already known in the prior art. These processes are, in general, mainly directed towards obtaining factor VIIIc of high purity, the von Willebrand factor being obtained as a byproduct. For example, the document EP-A-0,359,593 (CRTS Lille) describes a process for separating proteins from a fraction of human or animal plasma, according to which a factor VIIIc concentrate of high purity which is usable for the treatment of haemophilia A is obtained, as well as concentrates of fibrinogen, of von Willebrand factor and of fibronectin. According to this previous process, the factor VIIIc obtained is only partially freed from von Willebrand factor, and this constitutes a drawback of this process.

In the document FR 89/02,136 of the Applicant, a process has been described for manufacturing antihaemophilic factor (FVIIIc) having a very high purity, making it possible to obtain, as secondary constituents, von Willebrand factor, the method of purification of which was not described.

SUMMARY OF THE INVENTION

The main object of the present invention is to obtain von Willebrand factor of very high purity starting from this process previously described by the Applicant in the document FR 89/02 136.

The object of the present invention is to provide a von Willebrand factor of very high purity, by a simple manufacturing process enabling good reproducibility to be obtained as well as very large quantities to be processed on an industrial scale, while being relatively inexpensive.

The present invention enables this new technical problem to be solved for the first time in a manner which is simple, reproducible and satisfactory, and hence usable on an industrial scale, enabling large quantities to be processed without limitation of volume, in contrast to the previous techniques which are limited to the laboratory.

In addition, the invention produces a viral inactivation.

DESCRIPTION OF THE PREFERRED EMBODIMENTS

Thus, according to a first aspect, the present invention provides a process for manufacturing von Willebrand factor having a very high purity, largely devoid of antihaemophilic factor (FVIIIc), comprising a step of purification by ion exchange (an ion exchange) chromatography using a first chromatography column containing a gel, comprising a step of adsorption of only the antihaemophilic factor on the gel of the said first column, which factor will be desorbed later for the purpose of obtaining it in purified form, while the von Willebrand factor largely devoid of factor VIIIc is contained in the nonretained fraction and is then treated in order to obtain it in a purified form, characterised in that the nonretained fraction containing the von Willebrand factor is treated so as to decrease the ionic strength of the nonretained solution until an ionic strength corresponding to that which is obtained with a 0.1 to 0.15 M NaCl solution is obtained, and the von Willebrand factor is then adsorbed selectively on the gel of a second column, eluting the said non-retained solution of reduced ionic strength with a first elution solution which has an ionic strength substantially identical to that of the nonretained solution having reduced ionic strength; the von Willebrand factor adsorbed on the gel of the second column is then desorbed by means of a second elution solution of higher ionic strength than the first elution solution, a purified solution of von Willebrand factor of very high purity, largely devoid of antihaemophilic factor VIIIc and of inactivators such as Tween and TNBP, as well as of the main plasma contaminants, thereby being obtained.

According to an advantageous embodiment of the process according to the invention, the ionic strength of the non-retained solution is reduced by carrying out a diafiltration, preferably preceded by a concentration. This diafiltration is advantageously carried out against a third buffer solution, preferably permitting an intravenous injection. Such a third buffer solution for the diafiltration can have the following composition:

| | |
|---|---|
| NaCl | 100 mmol, |
| Tris | 20 mmol, |
| CaCl$_2$.2H$_2$O | 10 mmol, |
| L-arginine | 17 mmol, |
| L-lysine HCl | 20 mmol. |

This solution is also brought to pH 7, with 12 N concentrated HCl.

According to a particular feature of the invention, the concentration of the diafiltered solution is carried out so as to obtain between 30 and 40 units of von Willebrand factor:RCO (ristocetin cofactor).

According to a preferred variant of embodiment of the process according to the invention, the first elution solution which enables the von Willebrand factor to be adsorbed selectively on the gel of the second column has the following composition:

| | |
|---|---|
| NaCl | 100–150 mmol, |
| Tris | 20 mmol. |

This solution is brought to pH 6.6 with 12 N concentrated HCl.

According to another particular feature of the process according to the invention, a solution of the following composition:

| | |
|---|---|
| NaCl | 350 mmol, |
| Tris | 20 mmol, | is used as a second elution solution which enables the von Willebrand factor to be desorbed from the second column. This composition is brought to pH 6.6 with 12 N concentrated HCl.

According to another advantageous feature of the process according to the invention, the purification gel which is used in the second ion exchange chromatography column, for selectively adsorbing the von Willebrand factor, is a gel having the following essential features:

a gel for exchanging anionic type ions, based on crosslinked agarose, especially having a concentration of approximately 6%, in bead form. This gel is preferably of the type possessing quaternary amino groups, in particular at the end of a small spacer arm, for example of the $C_1$-$C_6$ alkylene type, linked to the agarose beads.

A gel which corresponds to these features and which is commercially available is known under the trade name Q Sepharose fast flow ® and marketed by the Swedish company Pharmacia, the beads of which have a diameter of 45–165 µm in the wet state.

It should be noted that this gel displays a good affinity with respect to von Willebrand factor, of the order of 50 units of von Willebrand factor:Rag per litre of gel.

According to a particular feature of the process according to the invention, a cryoprecipitate extracted from human plasma, which is dissolved, preferably by dissolution in water, advantageously with the addition of heparin, is used as a source of von Willebrand factor. The solution thereby obtained is treated with aluminium hydroxide. The proportion of incorporation of aluminium hydroxide is not critical and can vary within wide limits. It is preferable, however, to use a proportion greater than 10% by volume relative to the total volume of the starting solution. Currently preferred proportions are of the order of 15% by volume.

Advantageously a centrifugation is also carried out to separate the aluminum hydroxide from the starting solution, in order to free the latter from vitamin K-dependent factors. However, according to an advantageous variant of embodiment of the process according to the invention, the solution initially containing factor VIIIc as well as the von Willebrand factor can then be inactivated virally using a buffer solution containing a solvent/detergent mixture as described in the document EP-A-0,131,740 or U.S. Pat. No. A-4,540,573.

The virally inactivated, crude solution thereby obtained is then freed from factor VIIIc according to the method described in the previous document of the Applicant FR 89/02,136, which is incorporated herein by reference.

It will simply be noted that, before proceeding to a step of adsorption on a first ion exchange chromatography column containing a factor VIIIc-binding gel, a diafiltration of the crude solution is carried out using a buffer solution identical to that used for elution of the first column used for binding the factor VIIIc.

Selective adsorption of the factor VIIIc is carried out on this first column, while the von Willebrand factor is present in the non-retained eluted solution which is then treated according to the process of the present invention, which has just been described.

The factor VIIIc is then recovered as described in the abovementioned document of the Applicant FR 89/02,136.

As regards the preferred step of diafiltration of the non-retained eluted solution containing the von Willebrand factor, a membrane having a cut-off capability at 100,000, for example a Millipore reference 4PTHK type membrane of the company Millipore, is used.

Moreover, for the purpose of preservation of the eluted solution of von Willebrand factor of very high purity obtained by the process according to the invention, largely devoid of antihaemophilic factor VIIIc and displaying a specific activity of more than 50 in terms of von Willebrand factor:RCO per mg of protein, a sterilising filtration is carried out on a sterilising filter having a pore size of diameter 0.22 µm, and this sterilised, purified solution of von Willebrand factor is then introduced into conventional vials.

In a second aspect, the present invention also provides von Willebrand factor of very high purity, characterised in that it has been obtained by the process described above. The invention also covers von Willebrand factor of very high purity, characterised in that it is largely devoid of factor VIIIc, preferably having a factor VIIIc content of less than 2%. Preferably, the specific activity of the von Willebrand factor according to the invention is at least 50 von Willebrand:RCO units/mg of protein.

According to a third aspect, the present invention also covers a pharmaceutical composition, characterised in that it contains von Willebrand factor as obtained by the process according to the invention or as defined above. Preferably, this pharmaceutical composition contains von Willebrand factor in lyophilised form, which enables an injectable preparation to be prepared at the time of use.

The invention also covers a process for manufacturing a pharmaceutical composition, characterised in that von Willebrand factor largely devoid of factor VIIIc, advantageously having a factor VIIIc content of less than 2%, is used as active principle. Preferably, this von Willebrand factor is in lyophilised form which enables an injectable preparation to be prepared at the time of use.

Lastly, the invention covers a method for the treatment of mammals, including man, suffering from von Willebrand's disease, characterised in that a therapeutically active amount of von Willebrand factor largely devoid of factor VIIIc, advantageously having a factor VIIIc content of less than 2%, is administered to the said mammals, including man. According to a particular embodiment, the specific activity of the von Willebrand factor is at least 50 von Willebrand:RCO units/mg of protein. This von Willebrand factor is, according to a particular variant of embodiment, in the form of a preparation for parenteral injection, prepared at the time of use from a lyophilised form. With the von Willebrand factor obtained according to the present invention, the administration dose will customarily be from 30 to 40 units of vW:RCO/kg of body weight/day.

Other objects, features and advantages of the invention will become clearly apparent on reading the explanatory description which follows, done with reference to an example of embodiment given simply by way of illustration and which can hence in no way limit the scope of the invention. In this example, the percentages are given by weight except where otherwise stated.

EXAMPLE OF THE INVENTION 3 g of cryoprecipitate of human blood plasma, derived from 300 ml of human plasma, are dissolved in 3.2 times its volume of solution of limulus-negative, osmotically purified water to which heparin was added in the proportion of 3 international units per ml of solution, at laboratory temperature and with stirring for 2 h so as to produce complete dissolution.

After measurement of the final volume, aluminium hydroxide is added to this solution in the proportion of 15% by volume relative to the total volume of this solution in order to remove vitamin K-dependent factors. The mixture is left stirring for 5 min in order to achieve this adsorption of the vitamin K-dependent factors on the aluminium hydroxide.

The mixture is centrifuged at 6,000 g in order to separate the aluminium hydroxide from the solution.

The crude solution containing factor VIIIc as well as the desired von Willebrand factor is treated according to the process described in the documents EP-A-0,131,740 or U.S. Pat. No. A-4,540,573 so as to produce a viral inactivation.

A diafiltration of the crude solution containing factor VIIIc as well as von Willebrand factor is then carried out against a buffer solution which will then be used for equilibration and elution of the first chromatography column used for selectively adsorbing factor VIIIc, having the following composition:

| | |
|---|---|
| NaCl | 250 mmol, |
| Tris | 20 mmol, |
| $CaCl_2 \cdot 2H_2O$ | 10 mmol. |

This solution has been brought to pH 6.6 with 12 N concentrated HCl.

This diafiltration is carried out with twice the volume of the crude solution containing factor VIIIc as well as von Willebrand factor, the solution being inactivated by thereby removing most of the products which were used for the viral inactivation. The membrane used for the diafiltration is a Millipore reference 4PTHK membrane having a cut-off capability at 100,000. A crude solution containing factor VIIIc as well as von Willebrand factor is thereby obtained, the solution being inactivated, diafiltered and concentrated to 10 l of total solution.

It is checked that this solution concentrated to 10 l has substantially the same ionic strength as the elution buffer solution of the first chromatography column used for selectively adsorbing factor VIIIc. The chromatography column is, for example, a column 25 cm high by 40 cm in diameter into which 32 l of the company Pharmacia's Q Sepharose fast flow ® gel are introduced.

The gel has been equilibrated with the elution solution before carrying out the injection of the 10 l of crude solution containing factor VIIIc and von Willebrand factor, at the rate of 25 l/h for an injection of the elution buffer solution at the same flow rate until a protein peak is no longer observed in the outflow from the column, by checking with a spectrophotometer at 280 nm, this peak corresponding mainly to the von Willebrand factor, fibrinogen, albumin and $\gamma$-globulins which it is desired to collect separately for the purpose of recovering the von Willebrand factor.

After elution of the column with the elution buffer solution, the factor VIIIc has thereby been adsorbed selectively on this column. Moreover, the nonretained eluted solution contains the von Willebrand factor, fibrinogen, albumin and $\gamma$-globulins as well as the plasma inactivators, and has a volume of 80 to 100 litres.

The von Willebrand factor is separated selectively by the process according to the invention in the following manner:

In the first place, a diafiltration of the nonretained eluted solution containing the von Willebrand factor is carried out against a first buffer solution of the following composition:

| | |
|---|---|
| NaCl | between 100 and 150 mmol, preferably approximately 120 mmol, |
| Tris | 20 mmol. |

This solution is brought to a pH equal to 6.6 with 12 N concentrated HCl.

This solution is diafiltered with Millipore reference 4PTHK membrane having a cut-off capability at 100,000, under conditions producing a simultaneous concentration until a volume of 10 l of total solution is obtained.

It is checked that this solution of von Willebrand factor concentrated to 10 l has substantially the same ionic strength as the first elution buffer solution of the second chromatography column used for the selective adsorption of the von Willebrand factor.

The selective adsorption of the von Willebrand factor is then carried out on this second chromatography column containing the same gel as the first chromatography column used for the selective adsorption of factor VIIIc, but which has been equilibrated here to an ionic strength corresponding to that of the von Willebrand solution, which is between 100 and 150 mmol with respect to NaCl.

The eluted and unbound portion emerging from this second column essentially contains fibrinogen, fibronectin, albumin and $\gamma$-globulins as well as plasma inactivators, which are set on one side.

Moreover, the von Willebrand factor adsorbed on the column is collected by elution with a second elution solution having a higher ionic strength, of the following composition:

| | |
|---|---|
| NaCl | between 300 and 350 mmol, preferably approximately 350 mmol, |
| Tris | 20 mmol. |

This solution has been brought to pH 6.6 with 12 N concentrated HCl.

In this second chromatography column, specific for the binding of von Willebrand factor, it suffices to use 8 l of Pharmacia Q Sepharose fast flow ® gel on account of the much higher affinity of this gel with respect to von Willebrand factor.

This eluted solution containing the purified von Willebrand factor is now concentrated by diafiltering it against a third buffer solution having the following composition:

| | |
|---|---|
| NaCl | approximately 100 mmol, |
| Tris | 20 mmol, |
| $CaCl_2 \cdot 2H_2O$ | 10 mmol, |
| L-arginine | 17 mmol, |
| L-lysine HCl | 20 mmol, | this solution being brought to a pH equal to 7 with 12 N concentrated HCl.

This approach makes it possible to decrease the proportion of sodium to 100 mmol/l and to concentrate between 30 and 40 international units of von Willebrand factor:RCO per ml of solution. The diafiltration membrane which is used in this step is a Millipore reference 4PTHK membrane having a cut-off capability at 100,000.

A sterilising filtration of the solution of von Willebrand factor is then carried out on a sterilising membrane, for example that of the company Millipore reference Millidisk having a pore diameter of 0.22 μm.

A sterilised solution of von Willebrand factor of very-high purity is thereby obtained, which solution may be distributed in vials for storage of the products, in particular for the purpose of lyophilisation which may then be carried out in an altogether conventional manner. A von Willebrand factor having a specific activity of at least 50 von Willebrand:RCO units/mg of protein is thereby obtained.

This von Willebrand factor thereby constitutes a pharmaceutical composition of very great value, which makes it possible to inject a patient suffering from von Willebrand's disease with only the amounts of product necessary for treating this disease, thereby constituting a decisive technical advance.

In effect, by the invention, the yield of the process per litre of plasma is of the order of 350 international units of von Willebrand factor:RCO and is 600 international units of von Willebrand factor:RAg.

A further point to note is that this product displays very great stability over time. In particular, the activity of the von Willebrand factor has fallen by less than 5% after 24 hours following the taking up of the lyophilisate.

Rag means Ristocetin antigen.

We claim:

1. A process for the manufacture of von Willebrand factor having a specific activity of at least 50 expressed as von Willebrand : RCO units per milligram of proteins, and having a concentration of antihaemophilic factor (FVIIIc) of less than 2%, comprising the following steps:

(a) preparing a first buffered eluting solution having an ionic strength capable of separating factor VIIIc from a major part of the von Willebrand factor and main plasma contaminants, said first buffered eluting solution having a composition of:

| | |
   |---|---|
   | NaCl | 250 mM, |
   | Tris | 20 mM, |
   | CaCl$_2$.2H$_2$O | 10 mM, |
   | pH | 6.6. |

(b) preparing a crude solution of the factor VIIIc and von Willebrand factor from a cryoprecipitate having a substantially identical ionic strength to that of said first buffered eluting solution;

(c) equilibrating a first anionic exchange gel based on cross-linked agarose of a quaternary amine type in a first chromatography column with said first buffered eluting solution;

(d) selectively adsorbing the factor VIIIc on said first gel of said first column by passing said crude solution through said first gel of said first chromatography column and eluting said crude solution with said first buffered eluting solution, thereby having said factor VIIIc selectively adsorbed on the first gel of the first column, whereas the major portion of the von Willebrand factor is not adsorbed by said first gel in said first column;

(e) collecting the non retained fraction containing the major portion of the von Willebrand factor;

(f) treating the non retained fraction containing the von Willebrand factor to decrease the ioinic strength of said non retained fraction until an ionic strength, corresponding to that of a 0.10 to 0.15 M NaCl solution, is obtained;

(g) adsorbing said non retained fraction containing the von Willebrand factor with decreased ionic strength on a second anionic exchange get based on cross-linked agarose of a quaternary amine type in a second chromatography column, which has been equilibrated with a second eluting solution having the same decreased ionic strength as said non-retained fraction in step (f), thereby having said von Willebrand factor selectively adsorbed on the second gel of the second column, whereas the major portion of the contaminant proteins is not adsorbed;

(h) desorbing said adsorbed von Willebrand factor by eluting said second gel of said second column by using a third buffered eluting solution of ionic strength higher than that of said second buffered eluting solution; and (i) collecting the von Willebrand factor desorbed with said third buffered eluting solution, said von Willebrand factor having a concentration of factor VIIIc of less than 2%.

2. The process of claim 1, wherein the third eluting solution for desorbing von Willebrand factor from said second column comprises the following composition:

| | |
   |---|---|
   | NaCl | 350 mM, |
   | Tris | 20 mM, |
   | pH | 6.6. |

3. The process of claim 1, wherein the von Willebrand factor is concentrated and diafiltrated against a buffered solution permitting an intravenous injection.

4. The process of claim 1, wherein said first gel and said second gel are identical; said gels being in the form of agarose beads having short spacer arms linking the quaternary amine to the agarose beads.

5. The process of claim 4, wherein the spacer arms comprise $C_1$-$C_6$ alkylene moiety.

6. The process of claim 4, wherein said gel is Q-Sepharose fast flow ® (Pharmacia), the agarose beads having a diameter of 45 to 165 micrometers in a wet state.

7. The process of claim 1, wherein said cryoprecipitate extracted from human plasma is dissolved in a water solution containing heparin, said solution being then treated with aluminium hydroxide.

8. The process of claim 7, wherein the concentration of aluminium hydroxide is about 15% by volume relative to the total volume of the solution.

9. The process of claim 1, wherein the crude solution containing factor VIIIc and von Willebrand factor is virally inactivated.

10. The process of claim 1, wherein said von Willebrand factor is obtained in step (i) in a yield per liter of plasma of about 350 international units of von Willebrand factor: RCO.

* * * * *